US006358285B1

(12) United States Patent
Chen

(10) Patent No.: US 6,358,285 B1
(45) Date of Patent: Mar. 19, 2002

(54) MOTOR-DRIVEN PROSTHETIC PREHENSOR

(75) Inventor: Sen-Jung Chen, Taipei (TW)

(73) Assignee: Teh Lin Prosthetic & Orthopaedic Inc., Taipei (TW)

( * ) Notice: Subject to any disclaimer, the term of this patent is extended or adjusted under 35 U.S.C. 154(b) by 0 days.

(21) Appl. No.: 09/606,830

(22) Filed: Jun. 29, 2000

(51) Int. Cl.[7] ............................... A61F 2/54; A61F 2/68
(52) U.S. Cl. ........................................................ 623/64
(58) Field of Search .............................. 623/64, 63, 62, 623/61, 60, 65, 59, 44, 57; 475/197, 183; 294/88, 106

(56) References Cited

U.S. PATENT DOCUMENTS

| | | | | |
|---|---|---|---|---|
| 3,769,858 A | * | 11/1973 | Merell et al. .................. | 74/752 |
| 3,866,966 A | * | 2/1975 | Skinner, II ................... | 294/106 |
| 3,901,547 A | * | 8/1975 | Skinner, II ................... | 294/88 |
| 4,792,338 A | * | 12/1988 | Rennerfelt .................... | 623/64 |
| 4,923,477 A | * | 5/1990 | Horvath ........................ | 623/57 |
| 5,046,996 A | * | 9/1991 | Horvath ........................ | 475/197 |

FOREIGN PATENT DOCUMENTS

GB         2135012    *  8/1984   ................. 475/197

* cited by examiner

Primary Examiner—David H. Willse
Assistant Examiner—Alvin Stewart
(74) Attorney, Agent, or Firm—Ladas & Parry

(57) ABSTRACT

A motor-driven prosthetic prehensor includes an upright annular member and an annular retaining member having a friction wall that defines an accommodation space with a front wall of the annular member. A coupling sleeve member with a toothed rim is rotatably mounted on a transmission shaft disposed rotatably in the annular member, and has angularly spaced driving blocks extending into the accommodation space. A coupling member is mounted on and rotatable with the transmission shaft, and includes radially spaced driven spacer members that cooperate with the friction wall to define a plurality of chambers for receiving the driving blocks, and friction brakes that are slidable in the chambers between unobstructed position and braked positions. A coupling mechanism transmits rotation of the transmission shaft to drive a thumb member and a fingers assembly to move toward and away from each other so as to grasp or release an object.

6 Claims, 5 Drawing Sheets

MOTOR-DRIVEN PROSTHETIC PREHENSOR

BACKGROUND OF THE INVENTION

1. Field of the Invention

The invention relates to a motor-driven prosthetic prehensor, more particularly to a motor-driven prosthetic prehensor that is provided with a self-locking mechanism to enable the user to grasp an object tightly.

2. Description of the Related Art

A conventional motor-driven prosthetic prehensor generally includes a motor, a thumb member, and a fingers assembly. When the conventional prosthetic prehensor is used to grasp an object, a motor is operated to move the thumb member and the fingers assembly toward each other and is instantly stopped once the thumb member and the fingers assembly come into contact with the object to be grasped so as to prevent breaking or damaging of the object. However, when a conventional prosthetic prehensor as such is used to grasp a relatively heavy object, the thumb member and the fingers assembly may displace undesirably due to lack of a braking force, thus resulting in dropping of the object held therebetween.

SUMMARY OF THE INVENTION

Therefore, the main object of the present invention is to provide a motor-driven prosthetic prehensor that is equipped with a self-locking mechanism to permit firm grasping of an object.

Accordingly, the motor-driven prosthetic prehensor of the present invention comprises a mounting frame that includes an upright annular member and an annular retaining member. The upright annular member has a periphery, front and rear mounting walls opposite to each other in an axial direction, and an inner annular bearing wall disposed in the front mounting wall and confining an axial hole extending along a first axis parallel to the axial direction to communicate the front mounting wall with the rear mounting wall. The retaining member has an inner annular friction wall, which is disposed to extend forwardly from the periphery of the upright annular member. The friction wall and the front mounting wall together define an accommodation space. A transmission shaft is rotatably mounted on the bearing wall of the upright annular member, and includes a front segment extending forwardly of the front mounting wall, and a rear segment extending rearwardly of the rear mounting wall. A coupling sleeve member is rotatably mounted on the front segment of the transmission shaft about the first axis, and has front and rear major walls opposite to each other in the axial direction, a toothed rim wall joining and peripheral to the front and rear major walls, and a plurality of driving blocks angularly displaced from one another and disposed on the rear major wall to extend rearwardly and axially into the accommodation space. A rotatable coupling member is mounted on and rotatable with the front segment of the transmission shaft, and is interposed between the rear major wall of the coupling sleeve member and the front mounting wall of the upright annular member. The coupling member includes a hub portion about the first axis and a plurality of driven spacer members that extend radially and outwardly from the hub portion, and that are angularly spaced apart from one another so as to cooperate with the friction wall of the retaining member to define a plurality of chambers for receiving the driving blocks of the coupling sleeve member, respectively. Each driving block is angularly spaced from a respective one of the driven spacer members by a guideway. A plurality of friction brake members are disposed respectively in the chambers, and are movable slidably along the guideways between an unobstructed position, where the friction brake members are pushed by the driving blocks on the rear major wall of the coupling sleeve member to move angularly and radially towards the first axis and to drive the driven spacer members and the transmission shaft to rotate in a clockwise or counterclockwise direction when the coupling sleeve member is rotated in the clockwise or counterclockwise direction such that the friction brake members steer clear of frictional contact with the friction wall of the retaining member, and a braked position, where the friction brake members are brought to engage and to be retained by the friction wall once the transmission shaft is hindered from rotating freely with the driving blocks. A plurality of biasing members are each disposed between a respective one of the friction brake members and a respective one of the driven spacer members to bias the respective friction brake member to move towards a respective driving block such that once the transmission shaft is hindered from rotating with the driving blocks, the biasing members will bias the respective friction brake member to move away from the respective driven spacer member and to move radially to engage the friction wall of the retaining member so as to arrest any further rotation of the coupling sleeve member in the clockwise or counterclockwise direction. A motor has an output shaft rotatably mounted on the mounting frame. A drive gear is mounted on the output shaft, and is disposed to mesh with the toothed rim wall of the coupling sleeve member so as to drive the coupling sleeve member to rotate. A thumb member is pivotally mounted on the mounting frame about a first pivoting axis. A fingers assembly is pivotally mounted on the mounting frame about a second pivoting axis, and is spaced apart from the thumb member in a direction transverse to the axial direction. A coupling mechanism is disposed to transmit driven rotation of the transmission shaft to drive the thumb member and the fingers assembly to turn about the first and second pivoting axes, respectively, and to move toward or away from each other so as to grasp or release an object.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
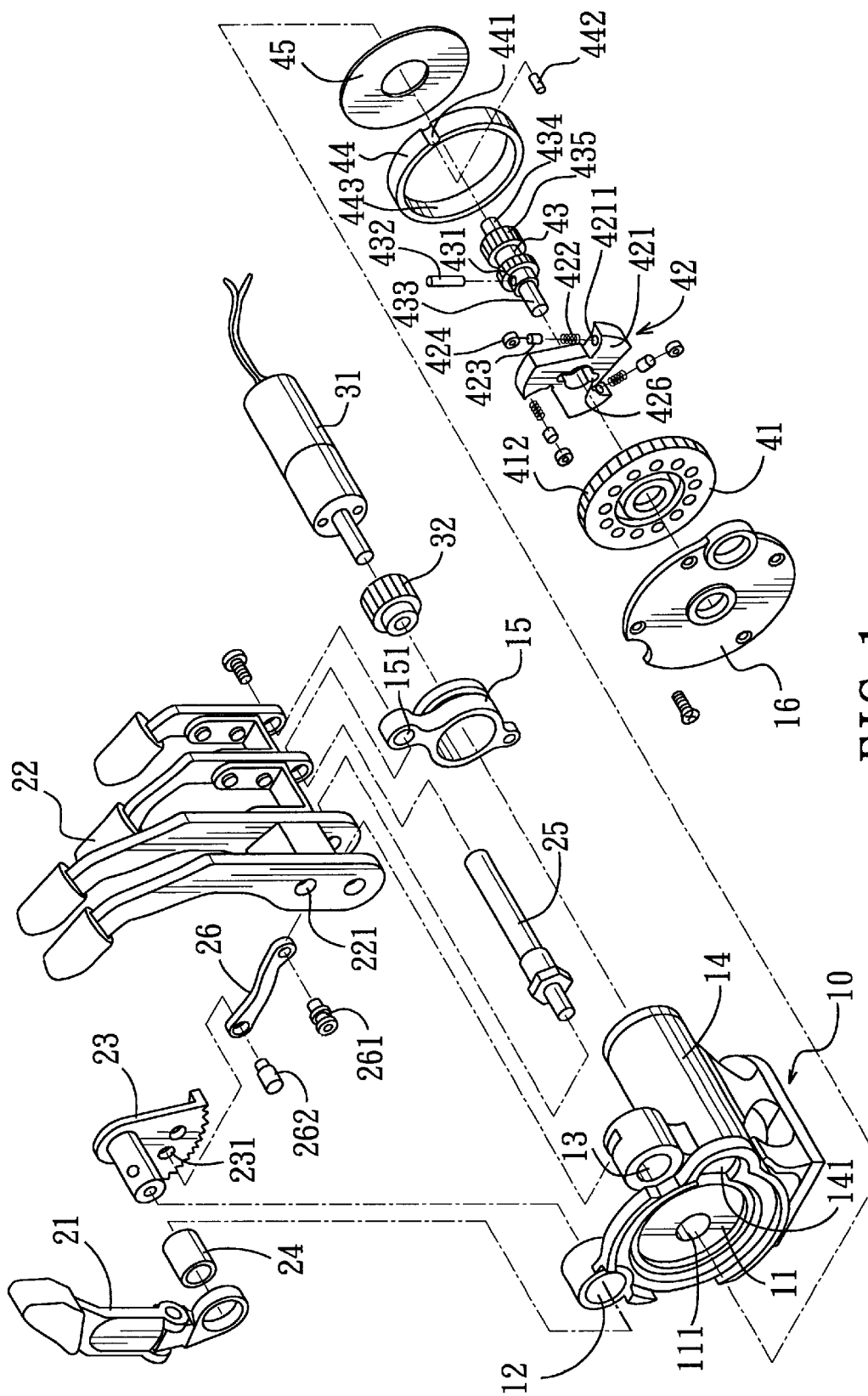
FIG. 1 is an exploded schematic view of a preferred embodiment of a motor-driven prosthetic prehensor according to the invention.

Before the present invention is described in greater detail, it should be noted that like elements are denoted by the same reference numerals throughout the disclosure.

Figure 2:
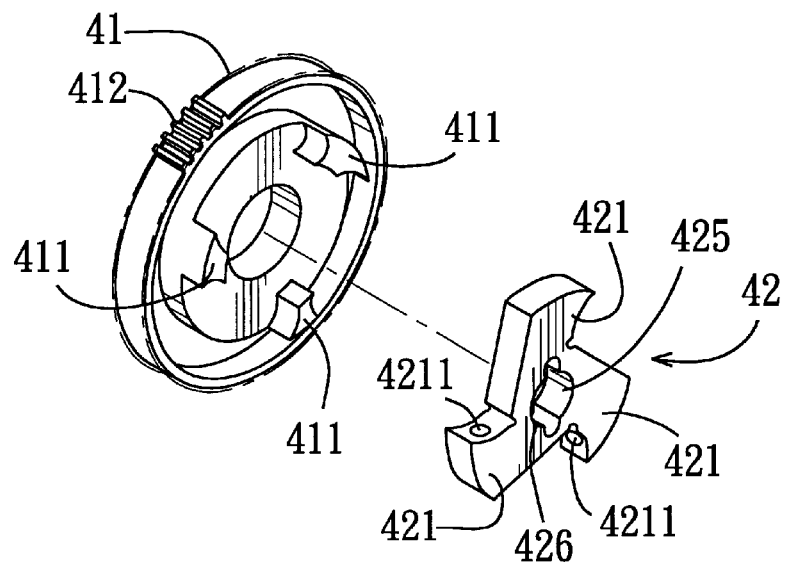
FIG. 2 is a schematic view illustrating a coupling sleeve member and a rotatable coupling member of the preferred embodiment.

Referring to FIGS. 1 and 2, the preferred embodiment of a motor-driven prosthetic prehensor according to the present invention is shown to comprise a mounting frame that includes an upright annular member 10 and an annular retaining member 44.

The upright annular member 10 has a periphery, a front mounting wall 11 and a rear mounting wall opposite to each other in an axial direction, and an inner annular bearing wall 111 disposed in the front mounting wall 11 and confining an axial hole extending along a first axis parallel to the axial direction to communicate the front mounting wall 11 with the rear mounting wall. A thumb member 21 is pivotally mounted in a thumb member mounting portion 12 on the upright annular member 10 about a first pivoting axis via a sleeve 24. A fingers assembly 22 is pivotally mounted in a fingers assembly mounting portion 13 on the upright annular member 10 about a second pivoting axis via a spindle 25, and is spaced apart from the thumb member 21 in a direction transverse to the axial direction. The thumb member 21 includes a thumb end distal to the first pivoting axis. The fingers assembly 22 includes a plurality of finger ends distal to the second pivoting axis. The upright annular member 10 further has a motor mounting portion 14 with a through hole 141 extending rearwardly from a lateral side thereof. A motor 31 is mounted in the motor mounting portion 14 with an output shaft thereof extending forwardly through the through hole 141. A connecting member 15 is locked to a rear end of the motor mounting portion 14, and has an upper mounting portion 151 for extension of a rear end of the spindle 25 therethrough. A drive gear 32 is mounted on the output shaft and extends through the connecting member 15.

The retaining member 44 has an inner annular friction wall 443, which is disposed to extend forwardly from the periphery of the upright annular member 10. The friction wall 443 and the front mounting wall 11 together define an accommodation space. A packing ring 45 may be disposed on the front mounting wall 11. In the case that the retaining member 44 is not integrally formed with the upright annular member 10, it may be secured fixedly to an inner surface of the front mounting wall 11 through inter-engagement of a curved indentation 441 formed in an outer periphery of the retaining member 44 and a positioning pin 442. As such, wearing of the inner surface of the front mounting wall 11 can be retarded, and rotation of the retaining member 44 can be prevented.

A transmission shaft 43 is rotatably mounted on the bearing wall 111 of the upright annular member 10, and includes a front segment 433 extending forwardly of the front mounting wall 11, and a rear segment 434 extending rearwardly of the rear mounting wall of the upright annular member 10.

Figure 3:
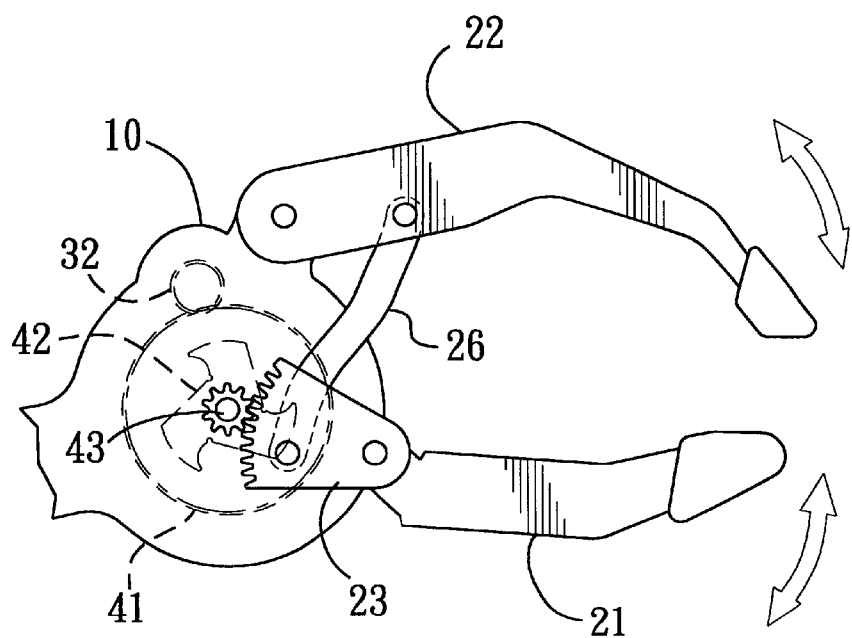
FIG. 3 is a schematic view illustrating operation of the preferred embodiment.

A coupling mechanism includes a transmission gear 435 mounted on and rotatable with the transmission shaft 43, and a segment gear 23 with a toothed segment pivotally mounted on the mounting frame 1 and meshed with the transmission gear 435 so as to transmit driven rotation of the transmission shaft 43 to drive the thumb member 21 and the fingers assembly 22 to turn about the first and second pivoting axes, respectively, and to move toward or away from each other so as to grasp or release an object, as shown in FIG. 3. The coupling mechanism further includes a linking arm 26 interconnecting the segment gear 23 at a position proximate to the toothed segment and the fingers assembly 22 at a position between the finger ends and the second pivoting axis by means of pins 262, 261 that engage respectively a gear hole 231 and a finger hole 221. The toothed segment is disposed on an opposite side of the first pivoting axis relative to the thumb end of the thumb member 21.

A coupling sleeve member 41 is rotatably mounted on the front segment 433 of the transmission shaft 43 about the first axis, and has front and rear major walls opposite to each other in the axial direction, a toothed rim wall 412 joining and peripheral to the front and rear major walls, and a plurality of driving blocks 411 (see FIG. 2) angularly displaced from one another and disposed on the rear major wall to extend rearwardly and axially into the accommodation space. The drive gear 32 meshes with the toothed rim wall 412 so as to drive the coupling sleeve member 41 to rotate.

Figure 4:
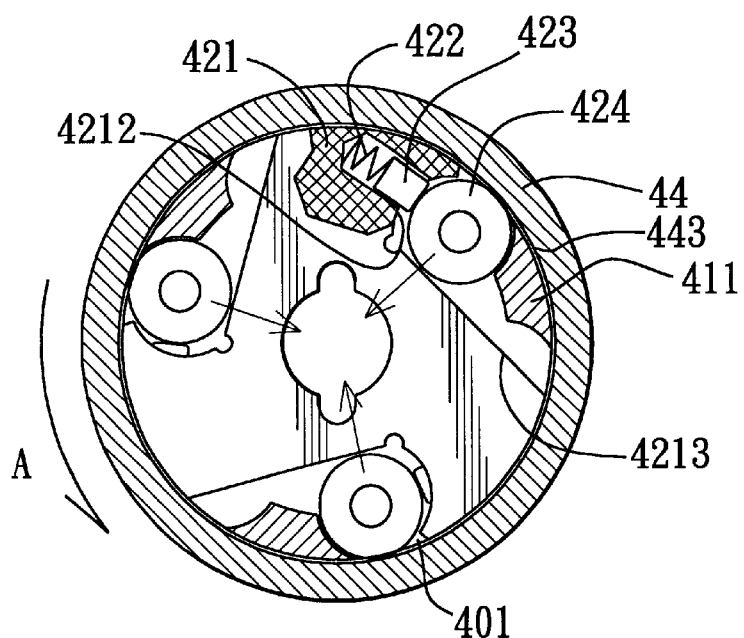
FIG. 4 is a schematic view illustrating the preferred embodiment in a released state.

A rotatable coupling member 42 is interposed between the rear major wall of the coupling sleeve member 41 and the front mounting wall 11 of the upright annular member 10, and includes a hub portion 426 about the first axis and a plurality of driven spacer members 421 that extend radially and outwardly from the hub portion 426, and that are angularly spaced apart from one another so as to cooperate with the friction wall 443 of the retaining member 44 to define a plurality of chambers that receive the driving blocks 411 of the coupling sleeve member 41, respectively. The coupling member 42 is mounted on the front segment 433 of the transmission shaft 43 for rotation therewith by means of a pin 432 passing through a through hole 431 in the front segment 433 and extending within a mounting hole 426 defined by the hub portion 426. With reference to FIG. 4, each driving block 411 is angularly spaced from a respective one of the driven spacer members 421 by a guideway 401. Each driven spacer member 421 has a cam surface 4213 extending in the axial direction and spaced apart from the friction wall 443 in radial directions by a respective one of the guideways 401.

A plurality of friction brake members 424 are disposed respectively in the chambers, and are movable slidably along the guideways 401 between an unobstructed position and a braked position. The cam surfaces 4213 are disposed to guide the friction brake members 424 to move between the unobstructed position and the braked position.

A plurality of biasing members 422 are each disposed in a blind hole 4211 formed in each of the driven spacer members 421 between a respective one of the friction brake members 424 and a respective one of the driven spacer members 421 to bias the respective friction brake member 424 to move towards the respective driving block 411. A roller 423 is further disposed between a respective one of the biasing members 422 and a respective one of the friction brake members 424.

Figure 5:
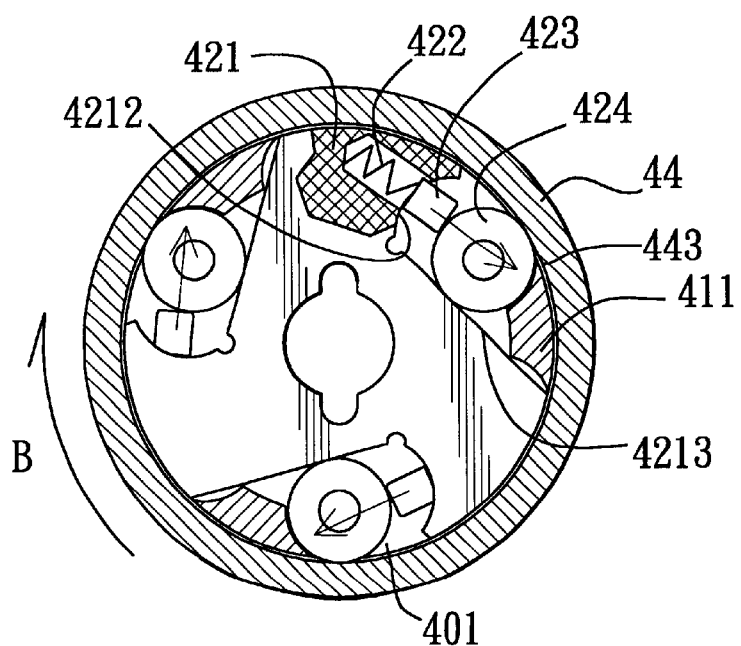
FIG. 5 is a schematic view illustrating operation of the preferred embodiment in a braking state.

Reference is made to FIGS. 4 and 5 illustrating operation of the embodiment. In the unobstructed position, the friction brake members 424 are pushed by the driving blocks 411 on the rear major wall of the coupling sleeve member 41 to move angularly and radially towards the first axis and to drive the driven spacer members 421 and the transmission shaft 43 to rotate in a direction A (counterclockwise or clockwise) when the coupling sleeve member 41 is rotated in the direction A such that the friction brake members 424 steer clear of frictional contact with the friction wall 443 of the retaining member 44, as shown in FIG. 4. In the braked position, the friction brake members 443 are biased by the respective biasing members 422 to move away from the respective driven spacer members 421, i.e., in an opposite direction B (clockwise or counterclockwise) and to move radially to engage the friction wall 443 of the retaining member 44 so as to arrest any further rotation of the coupling sleeve member 41 in the direction A once the transmission shaft 43 is hindered from rotating freely with the driving blocks 411. As such, when the thumb plate 21 and the fingers assembly 22 are driven to grasp a relatively heavy object, once the object is held therebetween, any further rotation of the coupling sleeve member 41 in a single direction is checked to prevent dropping of the object held.

Figure 6:
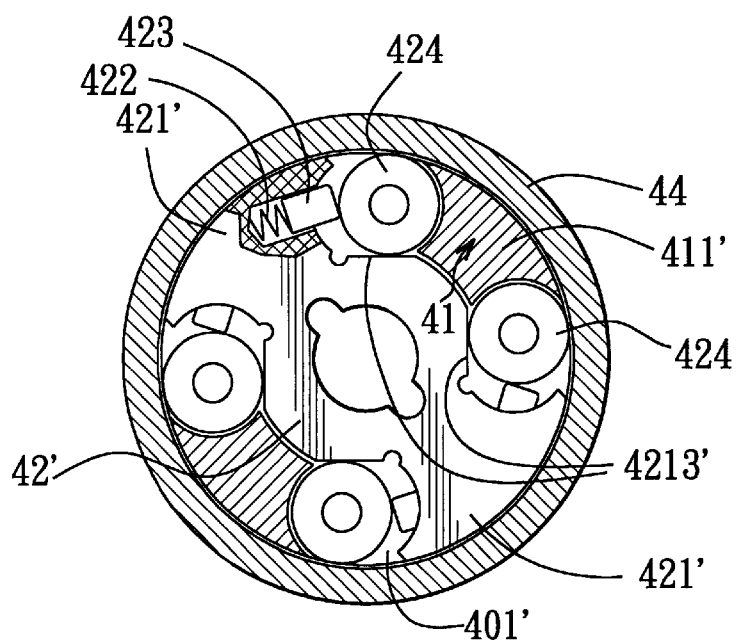
FIG. 6 is a schematic view illustrating operation of a modified embodiment of a motor-driven prosthetic prehensor according to the present invention.
Figure 7:
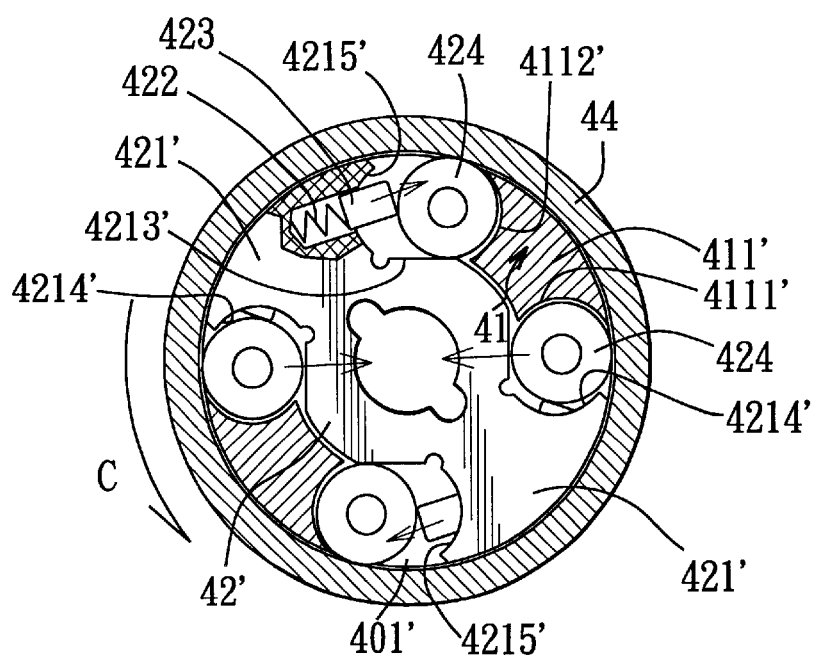
FIG. 7 is a schematic view illustrating the modified embodiment in a braking state when a coupling sleeve member is rotated counterclockwise.
Figure 8:
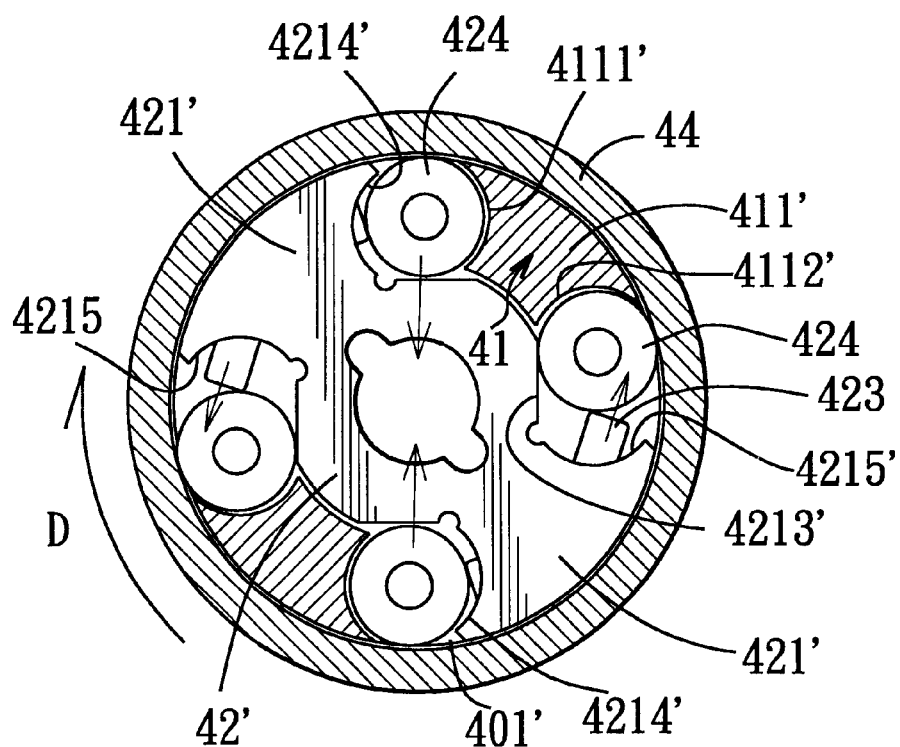
FIG. 8 is a schematic view illustrating the modified embodiment in a braking state when the coupling sleeve member is rotated clockwise.

Referring to FIGS. 6, 7 and 8, in a modified embodiment of the present invention, each of the driving blocks 411' includes a leading driving wall 4111' and a tailing driving wall 4112' extending respectively in the axial direction and opposite to each other angularly. The rotatable coupling member 42' includes two driven spacer members 421', each of which includes leading and tailing driven walls 4215', 4214' extending respectively in the axial direction, and opposite to each other angularly. The leading driven wall 4215' of one of the driven spacer members 421' and the tailing driven wall 4214' of the other of the driven spacer members 421' cooperate with the annular friction wall 443 of the retaining member 44 to define a chamber for receiving one of the driving blocks 411' so as to define with the tailing and leading driving walls of the respective one of the driving blocks 411' two guideways 401' to permit two respective ones of the friction brake members 424 to slide thereon. The two friction brake members 424 are biased towards the leading and tailing driving walls 4111' 4112' of the respective driving blocks 411' when the coupling sleeve member 41 is free to rotate in a clockwise or counterclockwise direction, as shown in FIG. 6. This embodiment differs from the previously described embodiment in that one of the friction brake members 424 in each chamber will engage the annular friction wall 443 of the retaining member 44 to check any further movement of the thumb member 21 and the fingers assembly 22 when the coupling sleeve member 41 is rotated in a direction C (counterclockwise) or a direction D (clockwise).

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

I claim:

1. A motor-driven prosthetic prehensor comprising:
   a mounting frame including:
      an upright annular member with a periphery, and having a front mounting wall and a rear mounting wall opposite to each other in an axial direction, and an inner annular bearing wall disposed in said front mounting wall, said inner annular bearing wall confining an axial hole extending along a first axis parallel to the axial direction to communicate said front mounting wall with said rear mounting wall, and
      an annular retaining member having an inner annular friction wall, which is disposed to extend forwardly from said periphery of said upright annular member, said inner annular friction wall and said front mounting wall cooperatively defining an accommodation space;
   a transmission shaft rotatably mounted on said inner annular bearing wall, and including a front segment extending forwardly of said front mounting wall, and a rear segment extending rearwardly of said rear mounting wall;
   a coupling sleeve member rotatably mounted on said front segment of said transmission shaft about the first axis, and having front and rear major walls opposite to each other in the axial direction; a toothed rim wall joining with and peripheral to said front and rear manor walls; and a plurality of driving blocks angularly displaced from one another and disposed on said rear major wall to extend rearwardly and axially into said accommodation space;
   a rotatable coupling member mounted on and rotatable with said front segment of said transmission shaft and interposed between said rear major wall of said coupling sleeve member and said front mounting wall of said upright annular member, said rotatable coupling member including a hub portion about the first axis and a plurality of driven spacer members extending radially and outwardly from said hub portion and angularly spaced apart from one another so as to cooperate with said inner annular friction wall of said retaining member to define a plurality of chambers that receive said plurality of driving blocks of said coupling sleeve member, respectively, each of said driving blocks being angularly spaced from a respective one of said driven spacer members by a guideway;
   a plurality of friction brake members disposed respectively in said chambers and movable slidably along said guideways between an unobstructed position, where said friction brake members are pushed by said driving blocks on said rear major wall of said coupling sleeve member to move angularly and radially towards the first axis and to drive said driven spacer members and said transmission shaft to rotate in a clockwise or counterclockwise direction when said coupling sleeve member is rotated in the clockwise or counterclockwise direction so that said friction brake members steer clear of frictional contact with said inner annular friction wall of said retaining member, and a braked position, where said friction brake members are brought to engage and to be retained by said inner annular friction wall once said transmission shaft is hindered from rotating freely with said driving blocks;
   a plurality of biasing members each disposed between a respective one of said friction brake members and a respective one of said driven spacer members to bias the respective one of said friction brake members to move towards a respective one of said driving blocks such that once said transmission shaft is hindered from rotating with said driving blocks, said biasing members will bias the respective one of said friction brake members to move away from the respective one of said driven spacer members and to move radially to engage said inner annular friction wall of said retaining member so as to arrest further rotation of said coupling sleeve member;
   a motor having an output shaft rotatably mounted on said mounting frame;
   a drive gear mounted on said output shaft and disposed to mesh with said toothed rim wall of said coupling sleeve member so as to drive said coupling sleeve member to rotate;
   a thumb member pivotally mounted on said mounting frame about a first pivoting axis;
   a fingers assembly pivotally mounted on said mounting frame about a second pivoting axis and spaced apart from said thumb member in a direction transverse to the axial direction; and a coupling mechanism disposed to transmit driven rotation of said transmission shaft to drive said thumb member and said fingers assembly to turn about the first and second pivoting axes, respectively, and to move toward or away from each other so as to grasp or release an object.

2. A motor-driven prosthetic prehensor according to claim 1, wherein each of said driven spacer members has a cam surface extending in the axial direction and spaced apart from said inner annular friction wall in a radial direction by a respective one of said guideways, said cam surface being disposed to guide the respective one of said friction brake members to move between the unobstructed and braked positions.

3. A motor-driven prosthetic prehensor according to claim 1, wherein each of said driving blocks includes a leading driving wall and a tailing driving wall extending respectively in the axial direction and opposite to each other angularly, and said rotatable coupling member includes two driven spacer members, each of said driven spacer members including leading and tailing driven walls extending respectively in the axial direction and opposite to each other angularly, said leading driven wall of one of said driven spacer members and said tailing driven wall of the other of said driven spacer members cooperating said annular friction wall of said retaining member to define a respective one of said chambers for receiving a respective one of said driving blocks so as to define with said tailing driving wall and said leading driving wall of the respective one of said driving blocks two guideways to permit two respective ones of said friction brake members to slide thereon.

4. A motor-driven prosthetic prehensor according to claim 3, wherein said two respective ones of said friction brake members are biased towards said leading and tailing driving walls of the respective one of said driving blocks.

5. A motor-driven prosthetic prehensor according to claim 1, wherein said coupling mechanism includes a transmission gear mounted on and rotatable with said transmission shaft, and a segment gear with a toothed segment pivotally mounted on said mounting frame and meshed with said transmission gear so as to transmit driven rotation of said transmission shaft to drive said thumb member and said fingers assembly.

6. A motor-driven prosthetic prehensor according to claim 5, wherein said thumb member includes a thumb end distal to said first pivoting axis, said toothed segment being disposed on an opposite side of the first pivoting axis relative to said thumb end; said fingers assembly includes a plurality of finger ends distal to said second pivoting axis; and said coupling mechanism further comprises a linking arm interconnecting said segment gear at a position proximate to said toothed segment and said fingers assembly at a position between said finger ends and said second pivoting axis.

* * * * *